US006509450B2

(12) United States Patent
Eyre

(10) Patent No.: US 6,509,450 B2
(45) Date of Patent: *Jan. 21, 2003

(54) IMMUNOASSAY FOR QUANTIFICATION OF C-TERMINAL TELOPEPTIDES OF TYPE I COLLAGEN IN HUMAN SERUM

(75) Inventor: David R. Eyre, Seattle, WA (US)

(73) Assignee: Washington Research Foundation, Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/812,658

(22) Filed: Mar. 19, 2001

(65) Prior Publication Data

US 2001/0031476 A1 Oct. 18, 2001

Related U.S. Application Data

(60) Continuation of application No. 09/501,823, filed on Feb. 10, 2000, now Pat. No. 6,204,367, which is a continuation of application No. 09/281,639, filed on Mar. 30, 1999, now Pat. No. 6,025,144, which is a continuation of application No. 09/209,864, filed on Dec. 11, 1998, now Pat. No. 5,962,236, which is a continuation of application No. 09/047,268, filed on Mar. 24, 1998, now Pat. No. 5,945,274, which is a continuation of application No. 08/771,452, filed on Dec. 20, 1996, now abandoned, which is a continuation of application No. 08/497,731, filed on Jun. 21, 1995, now Pat. No. 5,607,862, which is a continuation of application No. 08/195,323, filed on Feb. 10, 1994, now abandoned, which is a continuation of application No. 07/840,574, filed on Feb. 24, 1992, now abandoned, which is a continuation of application No. 07/592,511, filed on Oct. 3, 1990, now abandoned, which is a division of application No. 07/118,234, filed on Nov. 6, 1987.

(51) Int. Cl.$^7$ .............................................. C12P 21/08

(52) U.S. Cl. .................. 530/388.85; 530/344; 530/356; 530/391.1; 530/391.3; 435/7.1; 435/7.72; 435/7.94; 435/975; 436/526

(58) Field of Search .................. 435/7.1, 7.7, 7.72, 435/7.9, 7.91, 7.92, 7.94, 975; 436/526; 530/344, 356, 388.85, 389.1, 391.3, 391.1

(56) References Cited

U.S. PATENT DOCUMENTS

| | | |
|---|---|---|
| 3,600,132 A | 8/1971 | Goverde |
| 4,094,646 A | 6/1978 | Stern et al. |
| 4,312,853 A | 1/1982 | Timpl |
| 4,371,374 A | 2/1983 | Cerami et al. |
| 4,504,587 A | 3/1985 | Timpl et al. |
| 4,628,027 A | 12/1986 | Gay |
| 4,731,326 A | 3/1988 | Thompson et al. |
| 4,774,227 A | 9/1988 | Piez et al. |
| 4,973,666 A | 11/1990 | Eyre |
| 5,607,862 A | 3/1997 | Eyre |
| 5,945,274 A | 8/1999 | Eyre |
| 5,962,236 A | 10/1999 | Eyre |
| 6,025,144 A | 2/2000 | Eyre |

FOREIGN PATENT DOCUMENTS

| | | |
|---|---|---|
| CA | 1287801 | 2/1987 |
| EP | 128 041 | 6/1983 |
| WO | WO 88/08980 | 11/1988 |

OTHER PUBLICATIONS

Niemela, "Radioimmunoassays for Type III Procollagen Amino–Terminal Peptides In Humans," *Clinical Chemistry*, 31:1301–1304 (1985).

Sangiorgi, et al., "Isolation and partial characterization of the entire human proα1(II) collagen gene," *Nucleic Acids Research*, 13:2207–2225 (1985).

Loidl, et al., "Molecular cloning and carboxyl–propeptide analysis of human type III procollagen," *Nucleic Acids Research*, 12:9383–9394 (1984).

Wu and Eyre, "Identification of Hydroxypyridinium Cross–Linking Sites in Type II Collagen of Bovine Articular Cartilage," *Biochemistry*, 23:1850–1857 (1984).

Pierard, et al., "Radioimmunoassay for the Amino–Terminal Sequences of Type III Procollagen in Human Body Fluids Measuring Fragmented Precursor Sequences," *Analytical Biochemistry*, 141:127–136 (1984).

Rohde, et al., "Radioimmunoassay for type III procollagen peptide and its application to human liver disease," *European Journal of Clinical Investigation*, 9:451–459 (1979).

Russell, R.G.G., et al., "Biochemical Markers of Bone Turnover in Paget's Disease," *Metab. Bone Dis. & Rel. Res.*, 4 & 5:255–262 (1981).

Drinkwater, B.L., et al., "Bone Mineral Density After Resumption of Menses in Amenorrheic Atheletes," *JAMA*, 256:380–382 (1986).

Drinkwater, B.L., et al., "Bone Mineral Content of Amenorrheic and Eumenorrheic Athletes," the *New England Journal of Medicine*, 311:5; 277–281 (1984).

Fujimoto, D., "Evidence for Natural Existence of Pyridinoline Crosslink in Collagen," *Biochemical and Biophysical Research Communications*, 93:948–953 (1980).

Yamauchi, M. et al., "A Comparative Study of the Distribution of the Stable Crosslink, Pyridinoline, in Bone Collagens from Normal, Osteoblastoma, and Vitamin D–Deficient Chicks," *Biochemical and Biophysical Research Communications*, 102:59–65 (1981).

(List continued on next page.)

*Primary Examiner*—Jeffrey Stucker
(74) *Attorney, Agent, or Firm*—Christensen O'Connor Johnson Kindness PLLC

(57) ABSTRACT

An immunoassay kit for the quantification of degradation products of carboxy-terminal telopeptides of type I collagen in a human serum sample, including an antibody that is characterized by binding to at least one peptide derived from the carboxy-terminal telopeptide domain of type I collagen and isolatable from a urine sample of a patient with active Patet's disease.

4 Claims, 4 Drawing Sheets-

OTHER PUBLICATIONS

Figure 1:
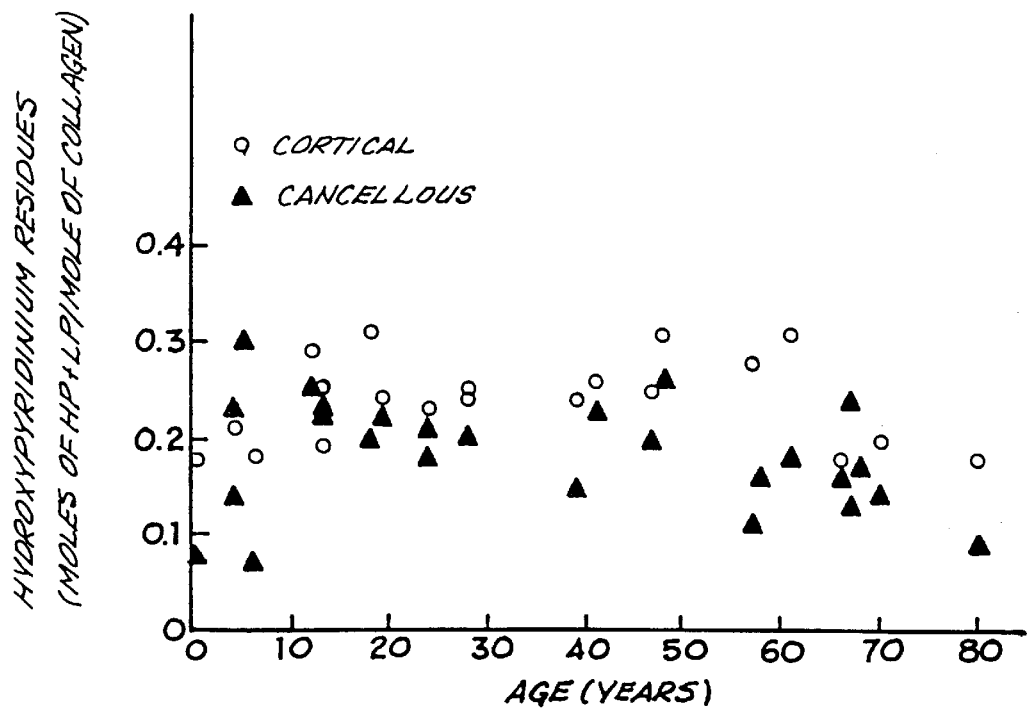

Kuboki, Y., et al., "Location of the Intermolecular Crosslinks in Bovine Dentin Collagen, Solubilization with Trypsin and Isolation of Cross–Link Peptides Containing Dihydroxylysinonorleucine and Pyridinoline," *Biochemical and Biophysical Research Communications*, 102:119–126 (1981).

Gunja–Smith, Z. and Boucek, R.J., "Collagen cross–linking compounds in human urine," *Biochemical Journal*, 197:759–762 (1981).

Tsuchikura, O., et al., "Pyridinoline Fluorescence in Cyanogen Bromide Peptides of Collagen," *Biochemical and Biophysical Research Communications*, 102:1203–1208 (1981).

Tsuda, M., et al., "Pyridinoline is a Real Moiety of Collagen," *Biochemical and Biophysical Research Communications*, 104:1407–1412 (1982).

Robins, S.P., "An enzyme–linked immunoassay for the collagen cross–link pyridinoline," *Biochemical Journal*, 207:617–620 (1982).

Banes, A.J., et al., "Nonmineralized and Mineralized Compartments of Bone: the Role of Pyridinoline in Nonmineralized Collagen," *Biochemical and Biophysical Research Communications*, 113:975–981 (1983).

Fujimoto, D., et al., "Analysis of Pyridinoline, a Cross–Linking Compound of Collagen Fibers, in Human Urine," *J. Biochem.*, 94:1133–1136 (1983).

Eyre, D.R., et al., "Corss–Linking in Collagen and Elastin," *Ann. Rev. Biochem.*, 53:717–748 (1984).

Light, N. and Bailey, A.J., "Collagen crosslinks: Location of pyridinoliine in type I collagen," *FEBS 2409*, 182:503–508 (1985).

Fujimoto, D., et al., "Pyridinoline, A Non–Reducible Crosslink of Collagen. Quantitative Determination, Distribution, and Isolation of a Crosslinked Peptide," *Chemical Abstracts* 89(11):148, (Sep. 11, 1978).

Fujimoto, D., et al., "Analysis of Pyridinoline, A Cross–Linking Compound of Collagen Fibers, in Human Urine," *Chemical Abstracts* 99(19):446–447, (Nov. 7, 1983).

Eyre, D.R., et al., "Quantitation of Hydroxypyridinium Crosslinks in Collagen by High–Performance Liquid Chromatography," *Analytical Biochemistry*, 137:380–388 (1984).

Robins, S.R., et al., "Measurement of the cross linking compound, pyridinoline, in urine as an index of collagen degradation in joint disease," *Annals of the Rheumatic Diseases*, 45:969–973 (1986).

Bernard, M.P., et al., "Nucleotide Sequences of Complementary Deoxyribonucleic Acids for the Proα1 Chain of Human Type I Procollagen. Statistical Evaluation of Structures that are Conserved During Evolution," *Biochemistry*, 22:5213–5223 (1983).

Goldstein, D., et al., "Simultaneous Measurement of DOPA, DOPAC, and Catecholamines in Plasma by Liquid Chromatography with Electrochemical Detection," *ESA Review*, vol. II, No. 1, pp. 2–11 (1986).

Chu, M–L., et al., "Human proα1(I) collagen gene structure reveals evolutionary conservation of a pattern of introns and exons," *Nature* 310(26):337–340 (1984).

Robins, S.P., et al., "Measurement of Hydroxypyridinium Crosslinks of Collagen as an Index of Bone Matrix Degradation," *An Abstract of a Paper*, Lake Garda, Italy (1987).

Kang, A.H. and Gross, J., "Amino Acid Sequence of Cyanogen Bromide Peptides from the Amino–Terminal Region of Chick Skin Collagen," *Biochemistry* 9:796–804 (1970).

Highberger, J.H., et al., "The Amino Acid Sequence of Chick Skin Collagen α1–CB7," *Biochemistry* 14(13):2872–2881 (1975).

Fietzek, P.P. and Kuhn, K., "The Covalent Structure of Collagen: Amino Acid Sequence of the N–Terminal Region of α2–CB5 from Rat Skin Collagen," *FEBS Letters* 36(3):289–291 (1973).

Dixit, S.N., et al., "Covalent Structure of Collagen: Amino Acid Sequence of α2–CB5 of Chick Skin Collagen Containing the Animal Collagenase Cleavage Site," *Biochemistry*, 18:3416–3422 (1979).

Dakkak, et al., "Modifications de l'hydroxyprolinurie peptidique au cours de la maladie de Paget et des ostéomes," *Ann. Biol. Clin.* 37:195–200 (1979).

Whittle, et al., "Biochemical investigation of possible lesions in human aorta that predispose to dissecting aneurysms: pyridinoline crosslinks," *Cardiovascular Research* 21:161–168 (1987).

Gunja–Smith, Z., "An Enzyme–Linked Immunosorbent Assay to Quantitate the Elastin Crosslink Desmosine in Tissue and Urine Samples," *Analytical Biochemistry* 147:258–264 (1985).

Schuppan, et al., "Radioimmunoassay for the Carboxy–terminal Cross–linking Domain of Type IV (Basement Membrane) Procollagen in Body Fluids," *J. Clin. Invest.* 78:241–248 (Jul. 1986).

Eyre, D., "Collagen Cross–Linking Amino Acids," In: *Methods in Enzymology*, vol. 144, pp. 115–139, Academic Press, Inc., 1987.

Eyre, et al., "Identification of urinary peptides derived from cross–linking sites in bone collagen in Paget's Disease," *Journal of Bone and Mineral Research*, 3, Supp. 1 (Jun. 1988).

Eyre, et al., "Reducible Crosslinks in Hydroxylysine–Deficient Collagens of a Heritable Disorder of Connective Tissue," *Proc. Nat. Acad. Sci. USA* 69(9):2594–2598 (Sep. 1972).

Eyre, et al., "Evidence for a previously undetected sequence at the carboxy–terminus of the al chain of chicken bone collagen," *Biochemical and Biophysical Research Communications* 48(3):720–726 (1972).

Eyre, et al., "The distribution of crosslinking aldehydes in al and α2 chains of chicken bone collagen," *Biochimica et Biophysica Acta* 278:206–210 (1972).

Eyre, et al., "Evidence for intramolecular crosslinks in chicken bone collagen: the isolation of peptides containing allysine aldol," *Biochimica et Biophysica Acta* 295:301–307 (1973).

Eyre, et al., "Analysis of a crosslinked peptide from calf bone collagen: evidence that hydroxylysyl glycoside participates in the crosslinks," *Biochemical and Biophysical Research Communications* 52(2):663–671 (1973).

Eyre, et al., "Isolation of crosslinked peptides from collagen of chicken bone,"*Biochem J.* 135:393–403 (1973).

Eyre, et al, "The hydroxypyridinium crosslinks of skeletal collagens: their measurement, properties and a proposed pathway of formation," *Biochemical and Biophysical Research Communications* 92(2):403–410 (1980).

Walters, et al., "Collagen Crosslinks in Human Dentin: Increasing Content of Hydroxypyridinium Residues with Age," *Calcif. Tissue Int.* 35:401–405 (1983).

Wu, et al., "Identification of Hydroxypyridinium Cross–Linking Sites in Type II Collagen of Bovine Articular Cartilage," *Biochemistry* 23:1850–1857 (1984).

Wu, et al., "Cartilage type IX collagen is cross–linked by hydroxypyridinium residues," *Biochemical and Biophysical Research Communications* 123(3):1033–1039 (1984).

Eyre, et al., "Collagen type IX: evidence for covalent linkages to type II collagen in cartilage," *FEB* 220(2):337–341 (1987).

Eyre, D.R., "Collagen: Molecular Diversity in the Body's Protein Scaffold," *Science* 207:1315–1322 (1980).

Eyre, D.R., "Collagen Stability Through Covalent Crosslinking," In: Pearson, et al., eds. *Advances in Meat Research, vol. 4, Collagen as a Food*. New York: Van Nostrand Reinhold, 1987.

Eyre, D.R., "Crosslink maturation in bone collagen," In: Veis, A., ed. the *Chemistry and Biology of Mineralized Connective Tissues*, Elsevier North Holland, Inc., 1981.

Eyre, D.R., "Collagen cross–linking," In: Akeson, W.H. et al., eds., *AAOS: Symposium on Heritable Disorders of Connective Tissue*, St. Louis: C.V. Mosby, 1982, pp. 43–58.

Eyre, et al., "Studies on the molecular diversity and cross–linking of cartilage collagen," In: Peyron, J.G., ed. *Osteoarthritis: Current Clinical and Fundamental Problems*, Paris, France: CIBA–GEIGY, 1984, p. 117–122.

Davison, et al., "The Effects of Acetic Acid on Collagen Cross–Link," *Connective Tissue Research* 1:205–216 (1972).

Fujimoto and Moriguchi, "Pyridinoline, a non–reducible crosslink of collagen," *Biochem.*, 83:863–867 (1978).

Macek and Adam, "Determination of collagen degradation products in human urine in osteoarthrosis," *Z. Rheumatol.* 46:237–240 (1987).

Eyre, D.R., "Evidence for intramolecular cross–links in chicken bone collagen: Isolation of peptides containing allysine aldol," *Chem. Abstracts*, 78(13):81202c (1973).

Kühn, Klaus, "Chemical Properties of Collagen," In: *Immunochemistry of the Extracellular Matrix*, vol. I, pp. 1–29, CRC Press, Inc., 1982.

Robins, "Cross–linking of collagen," *Biochem. J.* 215:167–172 (1983).

Robins and Duncan, "Cross–linking of collagen," *Biochem. J.* 215:175–182 (1983).

Robins and Duncan, "Pyridinium crosslinks of bone collagen and their location in peptides isolated from rat femur," *Biochem. et Biophys. Acta* 914:233–239 (1987).

Henkel, Werner, Glanville, Robert W., and Oreifendorf, Dieter, "Characterisation of a type–I collagen trimeric cross–linked peptide from calf aorta and its cross–linked structure," *Eur. J. Biochem* 165:427–436, 1987.

Kuivaniemi, et al., "Structure of a full–length cDNA clone for a prepro$\alpha$(I) chain of human type I procollagen," *Biochem. J.* 252:633–640 (1987).

Bernard, M.P. et al., Nucleotide sequences of complementary deoxyribonucleic acids for the pro$\alpha_1$ chain of human type I procollagen; statistical evaluation of structures that are conserved during evolution, *Biochemisty* 22:5213–5223 (1983).

Del Pozo, A.M., et al., "Binding of 1–Anilinonsphthalene–8–Sulfonic Acid to Type I Collagen," *Int. J. Peptide Protein Res.* 28:329–358 (1983).

Robins, S.P., Analysis of the Crosslinking Components in Collagen and Elastin, *Methods of Biochemical Analysis* 28:329–379 (1982).

Fujimoto, D., Isolation and Characterization of a Fluorescent Material in Bovine Achilles Tendon Collagen, *Biochemical and Biophysical Research Communications* 76(4):1124–1129 (1977).

Click and Bornstein, Isolation and Characterization of the Cyanogen Bromide Peptides from the $\alpha$1 and $\alpha$2 Chains of Human Skin Collagen, *Biochemistry* 9(24):4699–4706 (1970).

Dickson et al., Analysis of the promoter region and the N–propeptide domain of the human pro$\alpha$2(I) collagen gene, *Nucleic Acids Research* 13(10):3427–3438 (1985).

Fujimoro, E., "Ultraviolet light– and ozone–induced changes in pyridinoline, a trisubstitued 3–hydroxypyridinium crosslink of collagen," *Biochimica et Biophysica Acta* 828:104–106 (1985).

Sakura et al., "Photolysis of pyridinoline, a cross–linking amino acid of collagen, by ultraviolet light," *Can. J. Biochem.*60:525–529 (1982).

Sakura et al., "Electrochemical behavior of pyridinoline, a crosslinking amino acid of collagen," *J. Biochem.* 89:1541–1546 (1981).

Koob et al., Detection and Photolysis of Hydroxypyridinium Crosslinks in Cartilage Collagen *In Situ*, *Orthopaedic Transactions* 7(2):251–252 (1983).

Baurain et al., "Photolysis of desmosine and isodesmosine by ultraviolet light," *Eur. J. Biochem* 67:155–164 (1976).

Becker, U., Timpl, R., and Kuhn, K., "Carboxyterminal Antigenic Determinants of Collagen from Calf Skin: Localization within Discrete Regions of the Nonhelical Sequences," *Eur. J. Biochem.* 28:221–231 (1972).

Lane et al., "Immunofluorescent Localization of Structural Collagen Types in Endochondral Fracture Healing," *Orthopaedic Transactions*, VI(2):236 (1982).

Kuhn, K., "The Classical Collagens: Types I, II, and III," *In: Structure and Function of Collagen Types* (1987).

Rauterberg, J., "The C–Terminal Non–Helical Portion of the Collagen Molecule," *Clin. Ortho. Rel. Res.* 97:196–212 (1973).

Davril et al., "Photolysis of crosslinked peptides from elastin of porcine aorta," *FEBS Letters*, 98(1):128–134 (1979).

Fuller, F. and Boedtker, H., "Sequence Determinatin and Analysis of the 3' Region of Chicken Pro–$\alpha$1(I) and Pro–a __(I) Collagen Messenger Ribonucleic Acids Including the Carboxy–terminal Propeptide Sequences," *Biochemistry* 20:996–1006 (1981).

Gunja–Smith & Boucek, "Desmosines in human urine," *Biochem. J.* 193:915–918 (1981).

Kiviriko, Int Rev Connect Tissue Res 5:93–163, 1970.

Tellerova et al., "Determination of larger urinary peptides in osteoarthrosis by high–performance liquid chromatography," *Scand J Rheumatology* 15:52–56 (1986).

Adam, M. and Z. Deyl, "Altered expression of collagen phenotype in osteoarthrosis," *Clinica Chimica Acta.*, 133:25–32 (1983).

Johnstone et al., Immunochemistry in Practice, Blackwell Scientific Publications, Oxford, U.K., 1987, pp. 48–65.

Furthmayer, Immunochemistry of the Extracellular Matrix, vol. 1, (CRC Press), pp. 143–178, 1982.

FLUORESCENCE 297nm, 380nm

FLUORESCENCE Ex 297nm, Em 380nm

IMMUNOASSAY FOR QUANTIFICATION OF C-TERMINAL TELOPEPTIDES OF TYPE I COLLAGEN IN HUMAN SERUM

CROSS REFERENCES TO RELATED APPLICATIONS

This is a continuation of prior application Ser. No. 09/501,823, filed Feb. 10, 2000 (U.S. Pat. No. 6,204,367), which is a continuation of application Ser. No. 09/281,639, filed Mar. 30, 1999 (U.S. Pat. No. 6,025,144), which is a continuation of application Ser. No. 09/209,864, filed Dec. 11, 1998 (U.S. Pat. No. 5,962,236), which is a continuation of application Ser. No. 09/047,268, filed Mar. 24, 1998 (U.S. Pat. No. 5,945,274), which is a continuation of application Ser. No. 08/771,452, filed Dec. 20, 1996 (abandoned), which is a continuation of application Ser. No. 08/497,731, filed Jun. 21, 1995 (U.S. Pat. No. 5,607,862), which is a continuation of application Ser. No. 08/195,323, filed Feb. 10, 1994 (abandoned), which is a continuation of application Ser. No. 07/840,574, filed Feb. 24, 1992 (abandoned), which is a continuation of application Ser. No. 07/592,511, filed Oct. 3, 1990 (abandoned), which is a divisional of application Ser. No. 07/118,234, filed Nov. 6, 1987 (U.S. Pat. No. 4,973,666), priority from the filing dates of which is hereby claimed under 35 U.S.C. § 120.

STATEMENT REGARDING FEDERALLY SPONSORED RESEARCH AND DEVELOPMENT

This invention was made with government support under one or more of grants AM 26489, AR 37318, AM 30774, and AR 36794 awarded by the National Institutes of Health. The government has certain rights in the invention.

BACKGROUND OF THE INVENTION

This invention relates to a method for assaying bone resorption rates. More specifically, it relates to a method for quantitating specific urinary cross-linking amino acids, and peptide fragments that contain those amino acids derived from degraded bone collagen.

Osteoporosis is the most common bone disease in man. Primary osteoporosis, with increased susceptibility to fractures, results from a progressive net loss of skeletal bone mass. It is estimated to affect 15-20 million individuals in the United States. Its basis is an age-dependent imbalance in bone remodelling, i.e., in the rates of synthesis and degradation of bone tissue. About 1.2 million osteoporosis-related fractures occur in the elderly each year including about 538,000 compression fractures of the spine, about 227,000 hip fractures and a substantial number of early fractured peripheral bones. Twelve to 20% of the hip fractures are fatal because they cause severe trauma and bleeding, and half of the surviving patients require nursing home care. Total costs from osteoporosis-related injuries now amount to at least $7 billion annually (Barnes, O. M., Science, 236, 914 (1987)). Osteoporosis is most common in postmenopausal women who, on average, lose 15% of their bone mass in the 10 years after menopause. This disease also occurs in men as they get older and in young amenorrheic women athletes. Despite the major, and growing, social and economic consequences of osteoporosis, no method is available for measuring bone resorption rates in patients or normal subjects. A major difficulty in monitoring the disease is the lack of a specific assay for measuring bone resorption rates.

Methods for assessing bone mass often rely on measuring whole-body calcium by neutron activation analysis or mineral mass in a given bone by photon absorption techniques. These measurements can give only long-term impressions of whether bone mass is decreasing. Measuring calcium balances by comparing intake with output is tedious, unreliable and can only indirectly appraise whether bone mineral is being lost over the long term. Other methods currently available for assessing decreased bone mass and altered bone metabolism include quantitative scanning radiometry at selected bone locations (wrist, calcaneus, etc.) and histomorphometry of iliac crest biopsies. The former provides a crude measure of the bone mineral content at a specific site in a single bone. Histomorphometry gives a semi-quantitative assessment of the balance between newly deposited bone seams and resorbing surfaces.

A urinary assay for the whole-body output of degraded bone in 24 hours would be much more useful. Mineral studies (e.g., calcium balance) cannot do this reliably or easily. Since bone resorption involves degradation of the mineral and the organic matrix, a specific biochemical marker for newly degraded bone products in body fluids would be the ideal index. Several potential organic indices have been tested. For example, hydroxyproline, an amino acid largely restricted to collagen, and the principal structural protein in bone and all other connective tissues, is excreted in urine. Its excretion rate is known to be increased in certain conditions, notably Paget's disease, a metabolic bone disorder in which bone turnover is greatly increased. For this reason, urinary hydroxyproline has been used extensively as an amino acid marker for collagen degradation. Singer, F. R., et al. (1978) *In: Metabolic Bone Disease, Vol. II* (eds. Avioli, L. V. and Krane, S. M.) pp. 489–575, Academic Press, New York.

Goverde (U.S. Pat. No. 3,600,132) discloses a process for determination of hydroxyproline in body fluids such as serum, urine, lumbar fluid and other intercellular fluids in order to monitor deviations in collagen metabolism. In particular, this inventor notes that in pathologic conditions such as Paget's disease, Marfan's syndrome, osteogenesis imperfecta, neoplastic growth in collagen tissues and in various forms of dwarfism, increased collagen anabolism or catabolism as measured by hydroxyproline content in biological fluids can be determined. This inventor measures hydroxyproline by oxidizing it to a pyrrole compound with hydrogen peroxide and N-chloro-p-toluenesulphonamide followed by colorimetric determination in p-dimethyl-amino-benzaldehyde.

In the case of Paget's disease, the increased urinary hydroxyproline probably comes largely from bone degradation, hydroxyproline, however, generally cannot be used as a specific index. Much of the hydroxyproline in urine may come from new collagen synthesis (considerable amounts of the newly made protein are degraded and excreted without ever becoming incorporated into tissue fabric), and from turnover of certain blood proteins as well as other proteins that contain hydroxyproline. Furthermore, about 80% of the free hydroxyproline derived from protein degradation is metabolized in the liver and never appears in the urine. Kiviriko, K. I. (1970) *Int. Rev. Connect. Tissue Res.* 5, 93, and Weiss, P. H. and Klein, L. (1969) *J. Clin. Invest.* 48, 1.

Hydroxylysine and its glycoside derivatives, both peculiar to collagenous proteins, have been considered to be more accurate than hydroxyproline as markers of collagen degradation. However, for the same reasons described above for hydroxyproline, hydroxylysine and its glycosides are probably equally non-specific markets of bone resorption. Krane, S. M. and Simon, L. S. (1981) *Develop. Biochem.* 22, 185.

In addition to amino acids unique to collagen, various non-collagenous proteins of bone matrix such as osteocalcin, or their breakdown products, have formed the basis of immunoassays aimed at measuring bone metabolism. Price, P. A. et al. (1980) *J. Clin. Invest.* 66, 878, and Gundberg, C. M. et al. (1984) *Meth. Enzymol.* 107, 516. However, it is now clear that bone-derived non-collagenous proteins, though potentially a useful index of bone metabolic activity are unlikely, on their own, to provide quantitative measures of bone resorption. The concentration in serum of osteocalcin, for example, fluctuates quite widely both normally and in metabolic bone disease. Its concentration is elevated in states of high skeletal turnover but it is unclear whether this results from increased synthesis or degradation of bone. Krane, S. M., et al. (1981) *Develop. Biochem.* 22, 185, Price, P. A. et al. (1980) *J. Clin. Invest.* 66, 878, and Gundberg, C. M. et al. (1984) *Meth. Enzymol.* 107, 516.

COLLAGEN CROSS-LINKING

The polymers of most genetic types of vertebrate collagen require the formation of aldehyde-mediated cross-links for normal function. Collagen aldehydes are derived from a few specific lysine or hydroxylysine side-chains by the action of lysyl oxidase. Various di-, tri- and tetrafunctional cross-linking amino acids are formed by the spontaneous intra- and intermolecular reactions of these aldehydes within the newly formed collagen polymers; the type of cross-linking residue varies specifically with tissue type (see Eyre, D. R. et al. (1984) *Ann. Rev. Biochem.* 53: 717-748). Two basic pathways of cross-linking can be differentiated for the banded (67 nm repeat) fibrillar collagens, one based on lysine aldehydes, the other on hydroxylysine aldehydes. The lysine aldehyde pathway dominates in adult skin, cornea, sclera, and rat tail tendon and also frequently occurs in other soft connective tissues. The hydroxylysine aldehyde pathway dominates in bone, cartilage, ligament, most tendons and most internal connective tissues of the body, Eyre, D. R. et al. (1974) vida supra. The operating pathway is governed by whether lysine residues are hydroxylated in the telopeptide sites where, aldehyde residues will later be formed by lysyl oxidase (Barnes, M. J. et al. (1974) *Biochem. J.* 139, 461). The chemical structure(s) of the mature cross-linking amino acids on the lysine aldehyde pathway are unknown, but hydroxypyridinium residues have been identified as mature products on the hydroxylysine aldehyde route. On both pathways and in most tissues the intermediate, borohydride-reducible cross-linking residues disappear as the newly formed collagen matures, suggesting that they are relatively short-lived intermediates (Bailey, A. J. et al. (1971) *FEBS Lett.* 16, 86). Exceptions are bone and dentin, where the reducible residues persist in appreciable concentration throughout life, in part apparently because the rapid mineralization of the newly made collagen fibrils inhibits further spontaneous cross-linking interactions (Eyre, D. R. (1981) *In: The Chemistry and Biology of Mineralized Connective Tissues* (Veis, A. ed.) pp. 51-55, Elsevier, N.Y., York, and Walters, C. et al. (1983) *Calc. Tiss. Intl.* 35: 401-405).

Two chemical forms of 3-hydroxypyridinium cross-link have been identified (Formula I and II). Both compounds are naturally fluorescent, with the same characteristic excitation and emission spectra (Fujimoto, D. et al. (1977) *Biochem. Biophys. Res. Commun.* 76, 1124, and Eyre, D. R. (1981) *Develop. Biochem.* 22, 50). These amino acids can be resolved and assayed directly in tissue hydrolysates with good sensitivity using reverse phase HPLC and fluorescence detection. Eyre, D. R. et al. (1984) *Analyt. Biochem.* 137: 380-388.

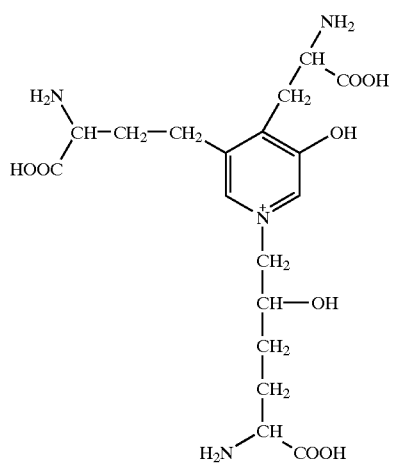

FORMULA I

In growing animals it has been reported that these mature cross-links may be concentrated more in an unmineralized fraction of bone collagen than in the mineralized collagen (Banes, A. J., et al. (1983) *Biochem. Biophys. Res. Commun.* 113, 1975). However, other studies on young bovine or adult human bone do not support this concept, Eyre, D. R. (1985) *In: The Chemistry and Biology of Mineralized Tissues* (Butler, W. T. ed.) p 105, Ebsco Media Inc., Birmingham, Alabama.

The presence of collagen hydroxypyridinium cross-links in human urine was first reported by Gunja-Smith and Boucek (Gunja-Smith, Z. and Boucek, R. J. (1981) *Biochem J.* 197: 759-762) using lengthy isolation procedures for peptides and conventional amino acid analysis. At that time, they were aware only of the HP form of the cross-link. Robins (Robins, S. P. (1982) *Biochem J.* 207: 617-620) has reported an enzyme-linked immunoassay to measure HP in urine, having raised polyclonal antibodies to the free amino acid conjugated to bovine serum albumin. This assay is intended to provide an index for monitoring increased joint destruc- tion that occurs with arthritic diseases and is based, according to Robins, on the finding that pyridinoline is much more prevalent in cartilage than in bone collagen. In more recent work involving enzyme-linked immunoassay, Robins reports that lysyl pyridinoline is unreactive toward antiserum to pyridinoline covalently linked to bovine serum albumin (Robins et al. (1986) *Ann. Rheum. Diseases* 45, 969–973). Robins' urinary index for cartilage destruction is based on the discovery that hydroxylysyl pyridinoline, derived primarily from cartilage, is found in urine at concentrations proportional to the rate of joint cartilage resorption. In principal, this index could be used to measure whole body cartilage loss, however, no information on bone resorption would be available.

A need therefore exists for a method that allows the measurement of whole-body bone resorption rates in humans. The most useful such method would be one that could be applied to body fluids, especially urine. The method should be sensitive, i.e., quantifiable down to 1 picomole and rapidly measure 24-hour bone resorption rates so that the progress of various therapies (e.g., estrogen) can be assessed.

SUMMARY OF THE INVENTION

A method for determining the absolute rate of bone resorption comprising quantitating the concentration of peptide fragments having 3-hydroxypyridinium cross-links derived from bone collagen resorption in a body fluid. The quantitating steps consists of contacting the body fluid with an immunological binding partner specific to a peptide fragment having 3-hydroxypyridinium cross-links derived from bone collagen resorption. In one embodiment of the invention, the body fluid is optionally purified prior to the contacting step. This purification step is selected from a number of standard procedures, including cartridge adsorption and elution, molecular sieve chromatography, dialysis, ion exchange, alumina chromatography, hydroxyapatite chromatography, and combinations thereof.

The invention also encompasses other methods for quantitating the concentration of peptide fragments having 3-hydroxypyridinium cross-links in a body fluid. These methods include electrochemical titration, natural fluorescence spectroscopy, and ultraviolet absorbance. Electrochemical titration may be conducted directly upon a body fluid without further purification. However, when this is not possible due to excessive quantities of contaminating substances, the body fluid is first purified prior to the electrochemical titration step. Suitable methods for purification prior to electrochemical detection include dialysis, ion exchange chromatography, alumina chromatography, molecular sieve chromatography, hydroxyapatite chromatography and ion exchange absorption and elution.

Fluorometric measurement of a body fluid containing 3-hydroxypyridinium cross-links is an alternative way of quantitating bone resorption. The fluorometric assay can be conducted directly on a body fluid without further purification. However, for certain body fluids, particularly urine, it is preferred that purification of the body fluid be conducted prior to fluorometric assay. This purification step consists of dialyzing an aliquot of urine against an aqueous solution thereby producing partially purified peptide fragments retained within the nondiffusate. The nondiffusate is then lyophylized, dissolved in an ion pairing solution and absorbed onto an affinity chromatography column. The chromatography column is washed with a volume of ion pairing solution and, thereafter, the peptide fragments are eluted from the column with an eluting solution. These purified peptide fragments are then hydrolyzed and the hydrolyzate is resolved chromatographically. Chromatographic resolution is conducted by either high-performance liquid chromatography or microbore high performance liquid chromatography.

The invention includes a peptide fragment derived from bone collagen substantially free from other human peptides obtained from a body fluid. The peptide fragment may contain 3-hydroxypyridinium cross-links, in particular, lysyl pyridinoline cross-links and hydroxylysyl pyridinoline cross-links.

A specific peptide fragment having a 3-hydroxpyridinium cross-link derived from the aminoterminal telopeptide domain of bone type I collagen has the following amino acid sequence.

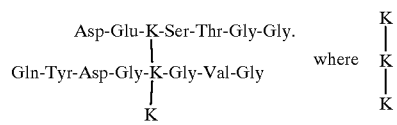

is hydroxylysyl pyridinoline or lysyl pyridinoline and, GLn is glutamine or wholly cyclized pyrrolidone carboxylic acid.

The invention also encompasses a peptide fragment containing 3-hydroxypyridinium cross-links derived from the carboxyterminal telopeptide domain of bone type I collagen. These carboxyterminal telopeptide sequences are cross-linked with either lysyl pyridinoline or hydroxylysyl pyridinoline. An example of such a peptide sequence is represented by the formula:

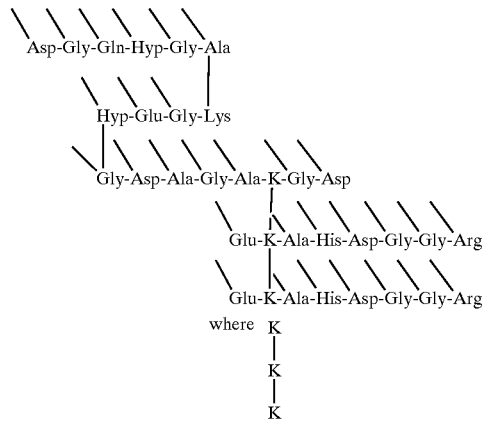

is hydroxylysyl or lysyl pyridinoline.

The invention includes a fused cell hydrid which produces monoclonal antibodies specific for the peptide fragment derived from bone collagen having 3-hydroxypyridinium cross-links. The invention also includes monoclonal antibodies produced by the fused cell hybrid including those antibodies coupled to a detectable marker. Examples of detectable markers include enzymes, chromophores, fluorophores, coenzymes, enzyme inhibitors, chemiluminescent materials, paramagnetic metals, spin labels and radio nucleotides. The invention includes a test kit useful for quantitating the amount of peptide fragments having 3-hydroxypyridinium cross-links derived from bone collagen resorption found in a body fluid comprising the monoclonal antibody specific for peptide fragments derived from bone collagen and containing 3-hydroxypyridinium cross-links. The monoclonal antibodies of this test kit may be coupled to the detectable markers described above.

DETAILED DESCRIPTION OF THE PREFERRED EMBODIMENTS

This invention is based on the discovery that both lysyl pyridinoline (LP) and hydroxylysyl pyridinoline (HP) peptide fragments derived from reabsorbed bone collagen are excreted in the urine without being metabolized. The invention is also based on the discovery that no other connective tissues contain significant levels of LP and that the ratio of HP to LP in mature bone collagen remains relatively constant over a person's lifetime.

Figure 2:
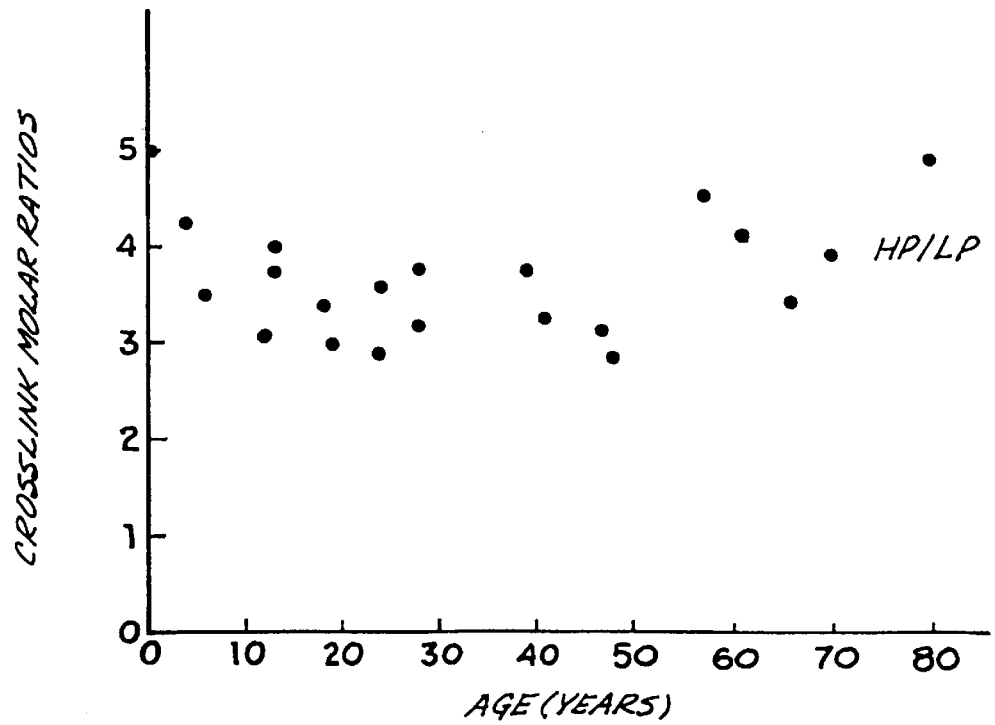

FIG. 1 compares the concentration of HP and LP in both cortical and cancellous human bone with age. It is observed that the concentration of HP plus LP cross-links in bone collagen reaches a maximum by age 10 to 15 years and remains reasonably constant throughout adult life. Furthermore, the ratio of HP to LP, shown in FIG. 2, shows little change throughout life, remaining constant at about 3.5 to 1. These baseline data demonstrate that the 3-hydroxypyridinium cross-links in bone collagen remains relatively constant and therefore that body fluids derived from bone collagen degradation will contain 3-hydroxypyridinium cross-linked peptide fragments at concentrations proportional to the absolute rate of bone resorption.

Since LP is the 3-hydroxypyridinium cross-link unique to bone collagen, the method for determining the absolute rate of bone resorption, in its simplest form, is based on quantitating the concentration of peptide fragments containing 3-hydroxypyridinium cross-links and preferably lysyl pyridinoline (LP) cross-links in a body fluid. As used in this description and in the appended claims, by quantitating is meant measuring by any suitable means, including but not limited to spectrophoto metric, gravimetric, volumetric, coulometric, immunometric, potentiometric, or amperometric means the concentration of peptide fragments containing 3-hydroxypyridinium cross-links in an aliquot of a body fluid. Suitable body fluids include urine, serum, and synovial fluid. The preferred body fluid is urine.

Since the concentration of urinary peptides will decrease as the volume of urine increases, it is further preferred that when urine is the body fluid selected, the aliquot assayed be from a combined pool of urine collected over a fixed period of time, for example, 24 hours. In this way, the absolute rate of bone resorption is calculated for a 24 hour period. Alternatively, urinary peptides may be measured as a ratio relative to a marker substance found in urine such as creatinine. In this way the urinary index of bone resorption would remain independent of urine volume.

In one embodiment of the present invention, monoclonal or polyclonal antibodies are produced which are specific to the peptide fragments containing lysyl pyridinoline cross-links found in urine. Peptide fragments may be isolated from the urine of any patient, however, it is preferred that these peptides are isolated from patients with Paget's disease, due to the high concentration of peptide fragments found in these patients.

ISOLATION OF URINARY PEPTIDES

Figure 3A:
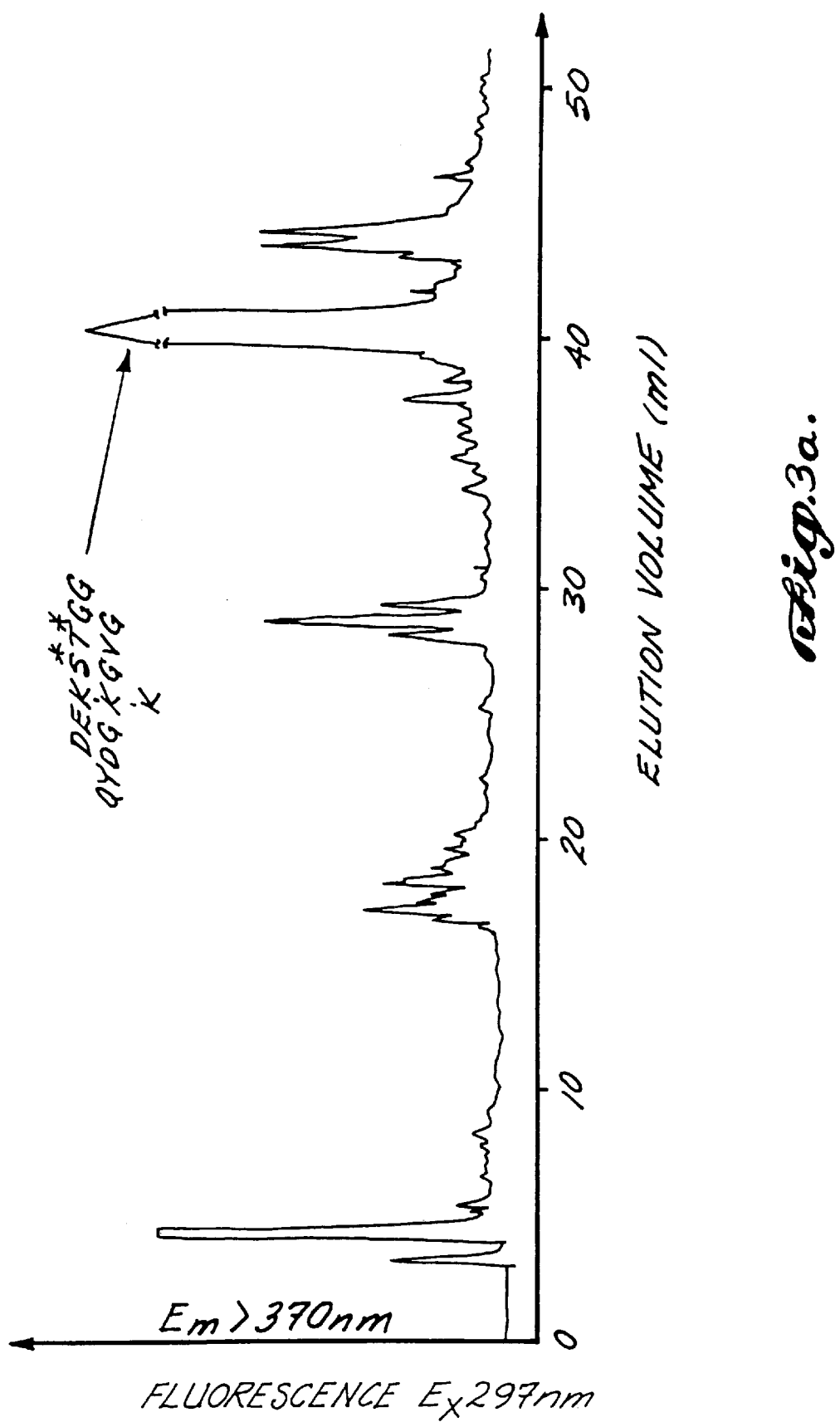

Urine from patients with active Paget's disease is dialyzed in reduced porosity dialysis tubing (>3,500 Spectra/Por®) at 4° C. for 48h to remove bulk solutes. Under these conditions the peptides of interest are largely retained. The freeze-dried non-diffusate is then eluted (200 mg aliquots) from a column (90 cm×2.5 cm) of polyacrylamide gel with a weight exclusion limit of 2,000 (Bio-Gel® P-2) (200–400 mesh) in 10% acetic acid at room temperature. A region of effluent that combines the cross-linked peptides is defined by measuring the fluorescence of collected fractions at 297 nm excitation/395 nm emission, and this pool is freeze-dried. Further resolution of this material is obtained on a column of polyacrylamide gel with a weight exclusion limit of 4,000 (Bio-Gel® P-4) (200–400 mesh, 90 cm×2.5 cm) eluted in 10% acetic acid. Two contiguous fraction pools are defined by monitoring the fluorescence of the eluant above. The earlier fraction is enriched in peptide fragments having two amino acid sequences that derive from the carboxyterminal telopeptide domain of the α1(I) chain of bone type I collagen linked to a third sequence derived from the triple-helical body of bone type I collagen. These three peptide sequences are cross-linked with 3-hydroxypyridinium. The overlapping later fraction is enriched in pepide fragments having an amino acid sequence that derives from the aminoterminal telopeptide domain of bone type I collagen linked throught a 3-hydroxypyridinium cross-links. Individual peptides are then resolved from each of the two fractions obtained above by ion-exchange HPLC on a TSK-GEL® DEAE-5-PW column (Bio-Rad® 7.5 cm×7.5 mm) eluting with a gradient of NaCl (0–0.2M) in 0.02 M Tris-HCl, pH 7.5 containing 10% (v/v) acetonitrile. The aminoterminal telopeptide-based and carboxyterminal telopeptide-based cross-linked peptides elute in a series of 3–4 peaks of fluorescence between 0.08 M and 0.15M NaCl. The carboxyterminal telopeptide-based cross-linked peptides elute first as a series of fluorescent peaks, and the major and minor aminoterminal telopeptide-based cross-linked peptides elute towards the end of the gradient as characteristic peaks. Each of these is collected, freeze-dried and chromatographed on a C-18 reverse phase HPLC column (Vydac® 218TP54, 25 cm×4.6 mm) eluted with a gradient (0–10%) of acetonitrile: n-propanol (3:1 v/v) in 0.01M trifluoroacetic acid. About 100–500 µg of individual peptide fragments containing 3-hydroxypyridinium cross-links can be isolated by this proceduce from a single 24h collection of Paget's urine. Amino acid compositions of the major isolated peptides confirmed purity and molecular sizes by the whole number stoichiometry of recovered amino acids. Aminoterminal sequence analysis by Edman degradation confirmed the basic core structures suspected from the sequences of the known cross-linking sites in type I collagen and from the matching amino acid compositions. The aminoterminal telopeptide sequence of the α2(I) chain was blocked from sequencing analysis due presumably to the known cylization of the aminoterminal glutamine to pyrrolidone carboxylic acid. A typical elution profile of aminoterminal telopeptides obtained by the above procedure is shown in FIG. 3a. The major peptide fragment obtained has an amino acid composition: $(Asx)_2(Glx)_2(Gly)_5$Val-Tyr-Ser-Thr, where Asx is the amino acid Asp or Asn and Glx is the amino acid Gln or Glu. The sequence of this peptide is represented by Formula III below.

Figure 3B:
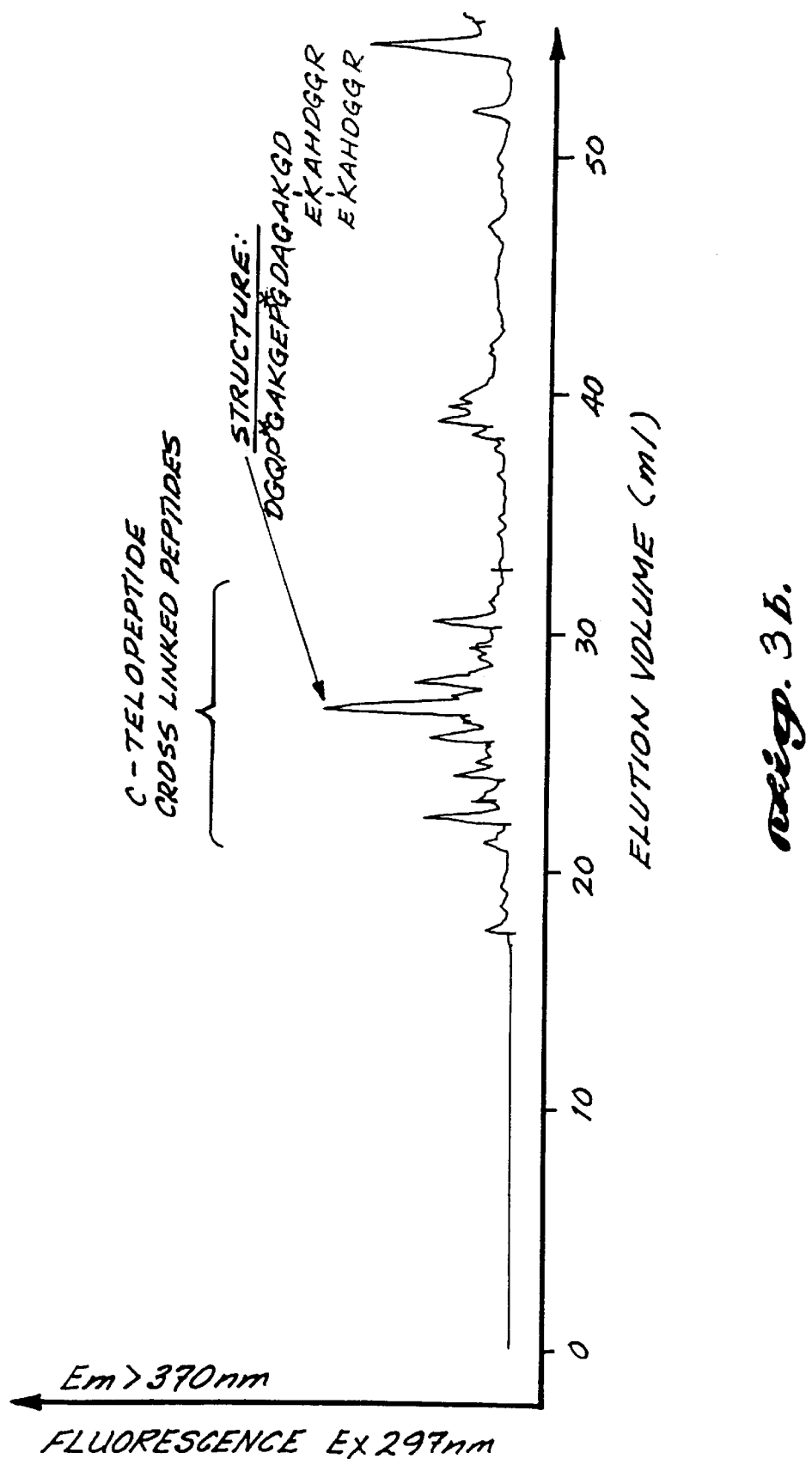

The carboxyterminal telopeptide-based cross-linked peptides resolved by reverse phase HPLC as described above are shown in FIG. 3b. As can be seen from this figure, these peptides are further resolved into a series of carboxyterminal telopeptides each containing the 3-hydroxypyridinium cross-links. The major peptide, shown in FIG. 3b, was analyzed as described above and was found to have the amino acid composition: $(Asp)_5(Glu)_4(Gly)_{10}(His)_2(Arg)_2(Hyp)_2(Ala)_5$. The sequence of this peptide is represented by formula IV below. It is believed that the other carboxyterminal telopeptide-based cross-linked peptides appearing as minor peaks in FIG. 3b represent additions and deletions of amino acids to the structure shown in Formula IV. Any of the peptides contained within these minor peaks are suitable for use as immunogens as described below.

FORMULA III

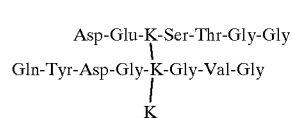

FORMULA IV

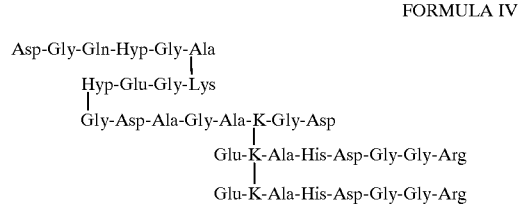

where

represents the HP or LP cross-linking amino acids, and

Gln represents glutamine or a wholly cyclized pyrrolidone carboxylic acid.

Equivalents of the peptides represented by the above structures include those cases where some variation in the urinary peptide structure accrues. Examples of variation include amino acid additions to the N and C termini of Formulae III and IV as well as some terminal amino acid deletions. Smaller peptide fragments of the molecule represented by Formula IV derived from bone readsorption are especially evident in urine. These are found in the minor peaks of the carboxytelopeptide fraction seen in FIG. 3b and can be identified by amino acid composition and sequence analysis. Furthermore, both the Ser and Thr residues of Formula III are occasionally conjugated to a small molecule. It is anticipated that antibodies produced to the haptens represented by Formulae III and IV will cross react with urinary peptides of slightly varied structure. In some situations it may be desirable to produce patient-specific antibodies to the urinary peptides derived from bone resorption. In these cases the same procedure described above is utilized to isolate urinary peptides whose structure may vary slightly from that represented by Formulae III and IV.

IMMUNOLOGICAL PROCEDURE FOR INDEXING BONE RESORPTION

Immunological binding partners capable of specifically binding to peptide fragments derived from bone collagen obtained from a physiological fluid can be prepared by methods well known in the art. The preferred method for isolating these peptide fragments is described above. By immunological binding partners as used herein is meant antibodies and antibody fragments.

Both monoclonal and polyclonal antibodies specifically binding the peptides represented by Formulae III and IV and their equivalents are prepared by methods known in the art. For example, *Laboratory Techniques in Biochemistry and Molecular Biology,* Campbell, A. M. (1986) Vol. 13 Elsevier, herein incorporated by reference. It is possible to produce antibodies to the above peptides or their equivalents as isolated. However, because the molecular weights of these peptide fragments are less than 5,000, it is preferred that the hapten be conjugated to a carrier molecule. Suitable carrier molecules include, but are not limited to, bovine serum albumin, ovalbumin, thyroglobulin, and keyhole limpet hemocyanin (KLH). Preferred carriers are thyroglobulin and KLH.

It is well known in the art that the orientation of the hapten, as it is bound to the carrier protein, is of critical importance to the specificity of the antiserum. Furthermore, not all hapten-protein conjugates are equally successful immunogens. The selection of a protocol for binding the particular hapten to the carrier protein therefore depends on the amino acid sequence of the urinary peptide fragments selected. For example, if the urinary peptide fragment represented by Formula III is selected, a preferred protocol would involve coupling this hapten to keyhole limpet hemocyanin (KLH), or other suitable carrier, with carbodiimide. This would ensure that most of the hapten would be conjugated through the Gly carboxyterminus, thereby presenting the preferred epitope, namely Tyr and 3-hydroxypyridinium cross-link, to the primed vertebrate antibody producing cells (e.g., B-lymphocytes).

Other urinary peptide fragments, depending on the source, may require different binding protocols. Accordingly, a number of binding agents may be suitably employed. These include, but are not limited to, carbodiimides, glutaraldehyde, mixed anhydrides, as well as both homobifunctional and heterobifunctional reagents (see for example the Pierce 1986-87 catalog, Pierce Chemical Co., Rockford, Ill.). Preferred binding agents include carbodiimides and heterobifunctional reagents such as m-Maleimidobenzyl N hydroxysuccinimide ester (MBS).

Methods for binding the hapten to the carrier molecule are known in the art. See for example *Laboratory Techniques in Biochemistry and Molecular Biology,* Chard, T. (1987) Vol. 6, Partz Elsevier, N.Y., herein incorporated by reference.

Either monoclonal or polyclonal antibodies to the hapten-carrier molecule immunogen can be produced. However, it is preferred that monoclonal antibodies (MAb) be prepared. For this reason it is preferred that immunization be carried out in the mouse. Immunization protocols for the mouse usually include an adjuvant. Examples of suitable protocols are described by Chard, T. (1987) vida supra. Spleen cells from the immunized mouse are harvested and homogenized and thereafter fused with cancer cells in the presence of polyethylene glycol to produce a fused cell hybrid which produces monoclonal antibodies specific to peptide fragments derived from bone collagen. Examples of such peptide frag- ments are represented by Formulae III and IV above. Suitable cancer cells include myeloma, hepatoma, carcinoma, and sarcoma cells. Detailed descriptions of this procedure, including screening protocols, protocols for growing selected hybrid cells and harvesting monoclonal antibodies produced by the selected hybrid cells are provided in Galfre, G. and Milstein, C. (1981) *Meth. Enzymol.* 73, 1. A preferred preliminary screening protocol involves the use of peptide fragments derived from bone collagen resorption and containing 3-hydroxypyridinium cross-links in a solid phase radioimmunoassay.

Immunological binding partners, especially monoclonal antibodies, produced by the above procedures, or equivalent procedures, are employed in various immunometric assays to quantitate the concentration of peptide fragments having 3-hydroxypyridinium cross-links derived from bone collagen resorption in body fluids. These immunometric assays comprise a monoclonal antibody or antibody fragment coupled to a detectable marker. Examples of suitable detectable markers include but are not limited to: enzymes, coenzymes, enzyme inhibitors, chromophores, fluorophores, chemiluminescent materials, paramagnetic metals, spin labels, and radionuclides. Examples of standard immunometric methods suitable for indexing bone resorption include, but are not limited to, enzyme linked immunosorbent assay ELISA (Ingvall, E. (1981) Meth. Enzymol. 70), radio-immunoassay (RIA), and "sandwich" Immuno radiometric assay (IRMA). In Its simplest form, these immunometric methods can be used to determine the absolute rate of bone resorption by simply contacting a body fluid with the immunological binding partner specific to a peptide fragment having 3-hydroxypyridinium cross-links derived from bone collagen resorption. It is preferred that the immunometric assays described above be conducted directly on untreated body fluids. Occasionally, however, contaminating substances may interfere with the assay necessitating partial purification of the body fluid. Partial purification procedures include, but are not limited to, cartridge adsorption and elution, molecular sieve chromatography, dialysis, ion exchange, alumina chromatography, hydroxyapatite chromatography and combinations thereof.

Test kits, suitable for use in accordance with the present invention, contain monoclonal antibodies prepared as described above that specifically bind to peptide fragments having 3-hydroxypyridinium cross-links derived from bone collagen resorption found in a body fluid. It is preferred that the monoclonal antibodies of this test kit be coupled to a detectable marker of the type described above.

ELECTROCHEMICAL PROCEDURE FOR INDEXING BONE RESORPTION

An alternative procedure for indexing bone resorption consists of measuring a physical property of the peptide fragments having 3-hydroxypyridinium cross-links. One such physical property suitable for indexing bone resorption relies upon electrochemical detection. This method consists of injecting an aliquot of a body fluid, such as urine, into an electrochemical detector poised at a redox potential suitable for detection of peptides containing the 3-hydroxypyridinium ring. The 3-hydroxypyridinium ring, being a phenol, is subject to reversible oxidation and therefore the electrochemical detector (e.g., Model 5100A Coulochem sold by esa 45 Wiggins Ave., Bedford, Mass.) is a highly desirable instrument suitable for quantitating the concentration of urinary peptides derived from bone adsorption. Two basic forms of electrochemical detector are currently commercially available: amperometric (e.g., BioAnalytical Systems) and coulometric (ESA, Inc., Bedford, Mass. 01730). Both are suitable for use in accordance with the present invention, however, the latter system is inherently more sensitive and therefore preferred since complete oxidation or reduction of the analyzed molecule in the column effluent is achieved. In addition, screening or guard electrodes can be placed "upstream" from the analytical electrode to selectively oxidize or reduce interfering substances thereby greatly improving selectivity. Essentially, the voltage of the analytical electrode is tuned to the redox potential of the sample molecule, and one or more pre-treatment cells are set to destroy interferents in the sample. In a preferred assay method, a standard current/voltage curve is established for standard peptides containing lysyl pyridinoline or hydroxylysyl pyridinoline in order to determine the proper voltage to set for optimal sensitivity. This voltage is then modified depending upon the body fluid, to minimize interference from contaminants and optimize sensitivity. Electrochemical detectors, and the optimum conditions for their use are known to those skilled in the art. Complex mixtures of body fluids can often be directly analyzed with the electrochemical detector without interference. Accordingly, for most patients no pretreatment of the body fluid is necessary. In some cases however, interfering compounds may reduce the reliability of the measurements. In such cases, pretreatment of the body fluid (e.g., urine) may be necessary.

Accordingly, in an alternative embodiment of the invention, a body fluid is first purified prior to electrochemically titrating the purified peptide fragments. The purification step may be conducted in a variety of ways including but not limited to; dialysis, ion exchange chromatography, alumina chromatography, hydroxyapatite chromatography, molecular sieve chromatography, or combinations thereof. In a preferred purification protocol, a measured aliquot (25 ml of a 24 hour urine sample is dialyzed in reduced porosity dialysis tubing to remove the bulk of contaminating fluorescent solutes. The non-diffusate is then lyophilized, redissolved in 1% heptafluorobutyric acid (HFBA), an ion pairing solution, and the peptides adsorbed on a Waters Sep-Pak C-18 cartridge. This cartridge is then washed with 5 ml of 196 HFBA, and then eluted with 3 ml of 50% methanol in 1% HFBA.

Another preferred method of purification consists of adsorbing a measured aliquot of urine onto an ion-exchange adsorption filter and eluting the adsorption filter with a buffered eluting solution. The eluate fractions containing peptide fragments having 3-hydroxypyridinium cross-links are then collected to be assayed.

Still another preferred method of purification employs molecular sieve chromatography. For example, an aliquot of urine is applied to a Bio-Gel P2 or Sephadex G-20 column and the fraction eluting in the 1000-5000 Dalton range is collected. It will be obvious to those skilled in the art that a combination of the above methods may be used to purify or partially purify urine or other body fluids in order to isolate the peptide fragments having 3-hydroxypyridinium cross-links. The purified or partially purified peptide fragments obtained by the above procedures may be subjected to additional purification procedures, further processed or assayed directly in the partially purified state. Additional purification procedures include resolving partially purified peptide fragments employing high performance liquid chromatography (HPLC) or microbore HPLC when increased sensitivity is desired. These peptides may then be quantitated by electrochemical titration. A preferred electrochemical titration protocol consists of tuning the redox potential of the detecting cell of the electrochemical detector (Coulochem Model 5100A) for maximum signal with pure HP. The detector is then used to monitor the effluent from a C-18 HPLC column used to resolve the partially purified urinary peptides.

FLUOROMETRIC PROCEDURE FOR INDEXING BONE RESORPTION

An alternative preferred method for quantitating the concentration of peptide fragments having 3-hydroxypyridinium cross-links is to measure the characteristic natural fluorescence of these peptide fragments. For those body fluids containing few naturally occurring fluorescent materials other than the 3-hydroxypyridinium cross-links, fluorometric assay may be conducted directly without further purification of the body fluid. In this case, peptide fragments are resolved by HPLC and the natural fluorescence of the HP and LP amino acid residues is measured at 395 nm upon excitation at 297 nm, essentially as described by Eyre, D. R., et al., Analyl. Biochem. 137, 380 (1984), herein incorporated by reference.

It is preferred, in accordance with the present invention, that the fluorometric assay be conducted on urine. Urine, however, usually contains substantial amounts of naturally occurring fluorescent contaminants that must be removed prior to conducting the fluorometric assay. Accordingly, urine samples are first partially purified as described above for electrochemical detection. This partially purified urine sample can then be fluorometrically assayed as described above. Alternatively, the HP and LP cross-linked peptides in the partially purified urine samples or other body fluids can be hydrolyzed in 6M HCl at about 108° C. for approximately 24 hours as described by Eyre, et al. (1984) vida supra. This process hydrolyzes the amino acids connected to the lysine precursors of "tripeptide" HP and LP cross-links, producing the free HP and LP amino acids represented by Formulae I and II. These small "tripeptides" are then resolved by the techniques described above, preferably by HPLC, and the natural fluorescence is measured (Ex 297 nm, Ex 390 nm).

Optionally, the body fluid (preferably urine) is passed directly through a C-18 reverse phase affinity cartridge after adding acetonitrile/methanol 5 to 10% V/V. The non-retentate is adjusted to 0.05-0.10M with a cationic ion-pairing agent such as tetrabutyl ammonium hydroxide and passed through a second C-18 reverse phase cartridge. The washed retentate, containing fluorescent peptides, from this second cartridge is eluted with acetonitrile:water (or methanol:water), dried and fluorescent peptides are analyzed by reverse phase HPLC or microbore HPLC using an anionic ion-pairing agent such as 0.01M trifluoroacetic acid in the eluant.

Figure 4B:
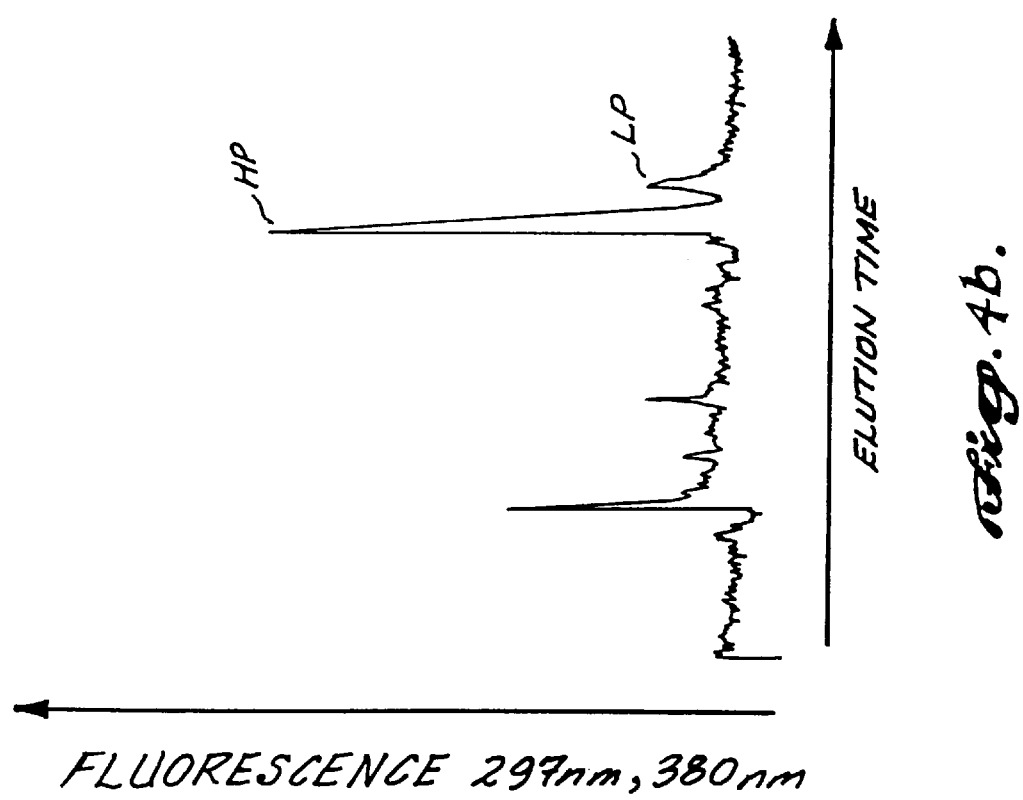
Figure 4A:
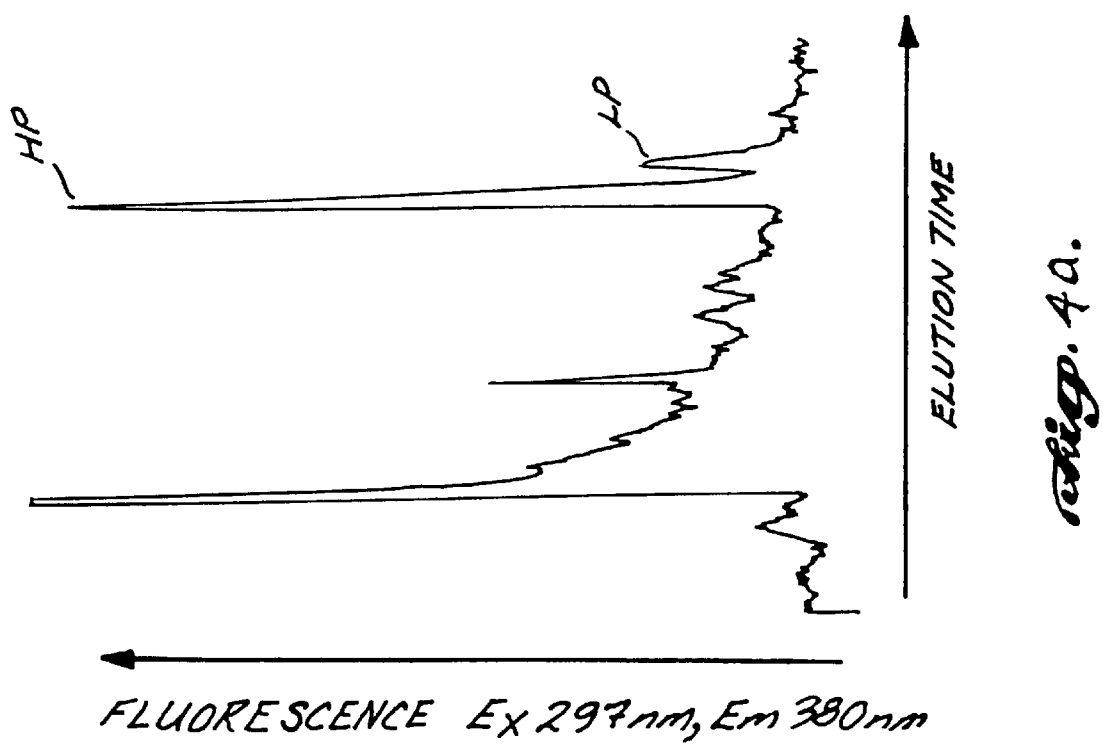

FIG. 4A displays the elution profile resolved by reverse phase HPLC of natural fluorescence for a hydrolysate of peptide fragments from normal human urine. Measurement of the integrated area within the envelope of a given component is used to determine the concentration of that component within the sample. The ratio of HP:LP found in normal human urine and urine from patients having Paget's disease, FIG. 4B, are both approximately 4.5:1. This is slightly higher than the 4:1 ratio found in bone itself (Eyre, et al., 1984). The higher ratio found in urine indicates that a portion of the HP fraction in urine may come from sources other than bone such as the diet, or other sources of collagen degradation, i.e., cartilage catabolism. It is for this reason that it is preferred that LP which derives only from bone be used to provide an absolute index of bone resorption. However, in the absence of excessive cartilage degradation such as in rheumatoid arthritis or in cases where bone is rapidly being absorbed, HP or a combination of HP plus LP may be used as an index of bone resorption.

While the invention has been described in conjunction with preferred embodi- ments, one of ordinary skill after reading the foregoing specification will be able to effect various changes, substitutions of equivalents, and alterations to the subject matter set forth herein. Hence, the invention can be practiced in ways other than those specifically described herein. It is therefore intended that the protection granted by Letters Patent hereon be limited only by the appended claims and equivalents thereof.

The embodiments of the invention in which an exclusive property or privilege is claimed are defined as follows:

1. An immunoassay kit for the quantification of degradation products of carboxy-terminal telopeptides of type I collagen in a human serum sample, comprising an antibody that is characterized by binding to at least one peptide derived from the carboxy- terminal telopeptide domain of type I collagen and having a 3-hydroxypyridinium cross-link, wherein the peptide is isolatable from a urine sample of a patient with active Paget's disease by a process which comprises the following steps:

dialyzing the urine sample in reduced porosity dialysis tubing (>3,500), and freeze-drying the non-diffusat;

chromatographing the dried material on a column of polyacrylamide gel with a weight exclusion limit of 2,000 in 10% acetic acid at room temperature, identifying a region of effluent the contains 3-hydroxypyridinium cross-linked peptides by measuring the fluorescence of collected fractions at 297 nm excitation/395 nm emission, and freez-drying the pooled fluorescent fractions;

chromatographing the dried material on a column of polyacrylamide gel with a weight exclusion limit of 4,000 eluted at 10% acetic acid, identifying two overlapping fraction pools by fluorescence of the eluant as measured above, and freeze-drying the earlier fraction pool;

chromatographing the dried material by ion-exchange HPLC on a DEAE-5-PW column eluted with a gradient of NaCl (0–0.2 M) in 0.02M Tris-HCl, pH 7.5 containing 10% (v/v) acetonitrile, identifying carboxy-terminal type I collagen telopeptide peaks that elute between 0.08M and 0.15M NaCl by fluorescence as measured above, and freeze-drying each peak;

chromatographing each dried peak on a C-18 reverse phase HPLC column eluted with a gradient (0–10%) of a acetonitrile:n-propanol (3.1 v/v) in 0.01M trifluoroacetic acid to isolate the individual peptides;

selecting isolated peptides that contain a 3-hydroxypyridinum cross-link derived from the carboxy-terminal telopeptide domain of type I collagen; and confirming that the antibody binds to at least one of the selected isolated peptides.

2. A sandwich immunoassay kit according to claim 1, wherein the first monoclonal antibody is coupled to a chemiluminescent material and the second monoclonal antibody is coupled to a coenzyme.

3. A sandwich immunoassay kit according to claim 2, comprising a paramagnetic material for coupling to the second monoclonal antibody.

4. A sandwich immunoassay kit for the quantification of degradation products of carboxy-terminal telopeptides of type I collagen in a human serum sample, comprising a first monoclonal antibody and a second monoclonal antibody that a characterized by binding to at least one peptide derived from the carboxy-terminal telopeptide domain of type I collagen and having a 3-hydroxypyridinium cross-link, wherein the peptide is isolatable from a urine sample of a patient with active Paget's disease by a process which comprises the following steps:

dialyzing the urine sample in reduced porosity dialysis tubing (>3,500), and freeze-drying the non-diffusate;

chromatographing the dried material on a column of polyacrylamide gel with a weight exclusion limit of 2,000 in 10% acetic acit at room temperature, identifying a region of effluent that contains 3-hydroxypyridinium cross-linked peptides by measuring the fluorescence of collected fractions at 297 nm excitation/395 nm emission, and freeze-drying the pooled fluorescent fractions;

chromatographing the dried material on a column of polyacrylamide gel with a weight exclusion limit of 4,000 eluted at 10% acetic acid, identifying two overlapping fraction pools by fluorescence of the eluant as measured above, and freeze-drying the earlier fraction pool;

chromatographing the dried material by ion-exchange HPLC on a DEAE-5-PW column eluted with a gradient of NaCl (0–0.2M) in 0.02M Tris-HCl, pH 7.5 containing 10% (v/v) acetonitrile, identifying carboxy-terminal type I collagen telopeptide peaks that elute between 0.08M and 0.15M NaCl by fluorescence as measured above, and freeze-drying each peak;

chromatographing each dried peak on a C-18 reverse phase HPLC column eluted with a gradient (0–10%) of a acetonitrile:n-propanol (3.1 v/v) in 0.01M trifluoroacetic acid to isolate the individual peptides;

selecting isolated peptides that contain a 3-hydroxypyridinium cross-link derived from the carboxy-terminal telopeptide domain of type I collagen; and confirming the the first and second monoclonal antibodies bind to at least one of the selected isolated peptides.

* * * * *

UNITED STATES PATENT AND TRADEMARK OFFICE
CERTIFICATE OF CORRECTION

PATENT NO. : 6,509,450 B2
DATED : January 21, 2003
INVENTOR(S) : D.R. Eyre

It is certified that error appears in the above-identified patent and that said Letters Patent is hereby corrected as shown below:

Title page,
Item [57], ABSTRACT,
Line 7, "Patet's Disease." should read -- Paget's disease. --

Column 1,
Lines 6-7, "Ser. No. 09/501,
823" should not break
Lines 23-24, "Pat. No. 4,973,
666)," should not break Column 2,
Line 66, "markets" should read -- markers --

Column 3,
Line 40, after "sites where" delete ","
Line 56, after "N.Y.," delete "York,"

Column 4,
Line 20, after the last line of the formula, insert centered on a separate line
-- hydroxylysyl pyridinoline (HP) --
Line 42, "destruc- tion" should read -- destruction --

Column 5,
Line 3, "steps consists of" should read -- steps consist of --
Line 64, "GLn" should read -- Gln --

Column 6,
Lines 6-23, 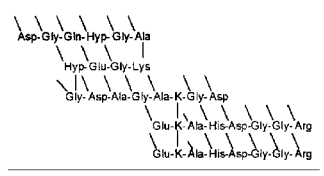 should read 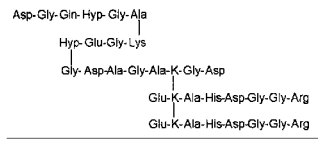

Line 25, "hydrid" should read -- hybrid --

UNITED STATES PATENT AND TRADEMARK OFFICE
CERTIFICATE OF CORRECTION

PATENT NO. : 6,509,450 B2
DATED : January 21, 2003
INVENTOR(S) : D.R. Eyre

It is certified that error appears in the above-identified patent and that said Letters Patent is hereby corrected as shown below:

Column 7,
Line 9, "spectrophoto metric," should read -- spectrophotometric, --.
Line 57, "pepide" should read -- peptide --
Line 60, "throught" should read -- through --
Line 60, "a 3-hydroxypyridinium cross-links" should read -- a 3-hydroxypyridinium cross-link. --
Line 67, "cross- linked" should read -- cross-linked --

Column 8,
Line 13, "proceduce" should read -- procedure --
Line 23, "cylization" should read -- cyclization --

Column 10,
Lines 13-14, "m-Maleimidobenzyl N hydroxysuccinimide" should read -- m-Maleimidobenzyl-N-hydroxysuccinimide --
Line 31, "frag-ments" should read -- fragments --
Lines 57-58, "Immuno radio-metric" should read -- Immunoradio-metric --

Column 11,
Line 26, "esa 45 Wiggins Ave., Bedford, Mass." should read -- ESA, Inc., Bedford, Mass. 01730. --
Line 62, "limited to;" should read -- limited to: --
Line 66, after "ml" insert -- ) --

Column 12,
Line 5, "196 HFBA," should read -- 1% HFBA, --
Line 33, "effluant" should read -- effluent --
Line 51, "Analyl." should read -- Anal. --

Column 13,
Line 37, "embodi- ments," should read -- embodiments, --
Line 51, "carboxy- terminal" should read -- carboxy-terminal --
Line 57, "non-diffusat;" should read -- non-diffusate; --
Line 64, "freez-drying" should read -- freeze-drying --

UNITED STATES PATENT AND TRADEMARK OFFICE
CERTIFICATE OF CORRECTION

PATENT NO. : 6,509,450 B2
DATED : January 21, 2003
INVENTOR(S) : D.R. Eyre

It is certified that error appears in the above-identified patent and that said Letters Patent is hereby corrected as shown below:

Column 14,
Line 36, "that a" should read -- that are --
Line 47, "acit at" should read -- acid at --

Column 16,
Line 2, "confirming the the" should read -- confirming that the --

Signed and Sealed this

Thirtieth Day of March, 2004

JON W. DUDAS
*Acting Director of the United States Patent and Trademark Office*